United States Patent
Schroecker et al.

(10) Patent No.: US 10,453,193 B2
(45) Date of Patent: Oct. 22, 2019

(54) METHODS AND SYSTEM FOR SHADING A TWO-DIMENSIONAL ULTRASOUND IMAGE

(71) Applicant: General Electric Company, Schenectady, NY (US)

(72) Inventors: Gerald Schroecker, Salzburg (AT); Daniel John Buckton, Salzburg (AT)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/587,733

(22) Filed: May 5, 2017

(65) Prior Publication Data

US 2018/0322628 A1  Nov. 8, 2018

(51) Int. Cl.
| G06K 9/00 | (2006.01) |
| G06T 7/00 | (2017.01) |
| G06T 7/50 | (2017.01) |
| A61B 8/08 | (2006.01) |
| A61B 8/00 | (2006.01) |
| A61B 8/06 | (2006.01) |

(52) U.S. Cl.
CPC ............ *G06T 7/0012* (2013.01); *A61B 8/488* (2013.01); *A61B 8/5207* (2013.01); *G06T 7/50* (2017.01); *A61B 8/06* (2013.01); *A61B 8/461* (2013.01); *A61B 8/54* (2013.01); *G06T 2207/10132* (2013.01)

(58) Field of Classification Search
CPC .................................................. G06T 7/0012
See application file for complete search history.

(56) References Cited

U.S. PATENT DOCUMENTS

| 5,860,931 | A | * | 1/1999 | Chandler | ................. | A61B 8/06 600/458 |
| 9,483,821 | B2 | | 11/2016 | Oh et al. | | |
| 2007/0014446 | A1 | * | 1/2007 | Sumanaweera | ......... | G06T 15/08 382/128 |
| 2009/0028406 | A1 | * | 1/2009 | Arditi | ...................... | A61B 8/06 382/131 |
| 2010/0290686 | A1 | * | 11/2010 | Canstein | ................ | A61B 6/481 382/131 |
| 2012/0265074 | A1 | * | 10/2012 | Na | .......................... | G06T 15/08 600/443 |
| 2013/0169641 | A1 | | 7/2013 | Schroecker | | |

(Continued)

OTHER PUBLICATIONS

"Volusion: Your Foundation for extraordinary vision in women's health ultrasound imaging," GE Website, Available Online at http://www3.gehealthcare.com/en/products/categories/ultrasound/voluson, Available as early as Apr. 15, 2015, as Retrieved on Jul. 6, 2017, 2 pages.

(Continued)

*Primary Examiner* — Oneal R Mistry
(74) *Attorney, Agent, or Firm* — McCoy Russell LLP (57) ABSTRACT

Various methods and systems are provided for shading a 2D ultrasound image, generated from ultrasound data, using a gradient determined from scalar values of the ultrasound image data. As one example, a method includes correlating image values of a dataset acquired with an ultrasound imaging system to height values; determining a gradient of the height values; applying shading to a 2D image generated from the dataset using the determined gradient; and displaying the shaded 2D image.

13 Claims, 5 Drawing Sheets
(1 of 5 Drawing Sheet(s) Filed in Color)

(56) References Cited

U.S. PATENT DOCUMENTS

| | | |
|---|---|---|
| 2014/0044325 A1 | 2/2014 | Ma et al. |
| 2014/0049542 A1 | 2/2014 | Engel |
| 2015/0209012 A1 | 7/2015 | Oh et al. |
| 2015/0213597 A1 | 7/2015 | Oh et al. |
| 2016/0350962 A1 | 12/2016 | Steen |
| 2017/0027648 A1 | 2/2017 | Hart et al. |
| 2017/0086785 A1 | 3/2017 | Bjaerum |
| 2017/0090571 A1 | 3/2017 | Bjaerum et al. |
| 2017/0188995 A1 | 7/2017 | Bruestle et al. |
| 2018/0082487 A1* | 3/2018 | Kiraly .................. A61B 5/7425 |
| 2018/0322628 A1 | 11/2018 | Schroecker et al. |

OTHER PUBLICATIONS

Perrey, C. et al., "Automatic Alignment of Ultrasound Volumes," U.S. Appl. No. 15/048,528, filed Feb. 19, 2016, 29 pages.

"Blinn-Phong shading model," Wikipedia Website, Available Online at https://en.wikipedia.org/wiki/Blinn%E2%80%93Phong_shading_model, Last modified Nov. 10, 2016, as Retrieved on Apr. 10, 2017, 5 pages.

"Phong reflection model," Wikipedia Website, Available Online at https://en.wikipedia.org/wiki/Phong_reflection_model, Last modified Feb. 21, 2017, as Retrieved on Apr. 10, 2017, 5 pages.

"Specular highlight," Wikipedia Website, Available Online at https://en.wikipedia.org/wiki/Specular_highlight, Last modified Feb. 27, 2017, as Retrieved on Apr. 10, 2017, 5 pages.

"Heightmap," Wikipedia Website, Available Online at https://en.wikipedia.org/wiki/Heightmap, Last modified Mar. 5, 2017, as Retrieved on Apr. 10, 2017, 3 pages.

"Heightmap," Unity Documentation Website, Available Online at https://docs.unity3d.com/Manual/StandardShaderMaterialParameterHeightMap.html, Jun. 19, 2017, 3 pages.

Eklund, A. et al., "Medical image processing on the GPU—Past, present and future," Medical Image Analysis, vol. 17, No. 8, Dec. 2013, Available Online Jun. 5, 2013, 22 pages.

"Method and System for Presenting Shaded Descriptors Corresponding With Shaded Ultrasound Images," U.S. Appl. No. 15/806,503, filed Nov. 8, 2017, 33 pages.

United States Patent and Trademark Office, Office Action Issued in U.S. Appl. No. 15/806,503, dated Feb. 26, 2019, 13 pages.

* cited by examiner

METHODS AND SYSTEM FOR SHADING A TWO-DIMENSIONAL ULTRASOUND IMAGE

FIELD

Embodiments of the subject matter disclosed herein relate to applying shading to a two-dimensional ultrasound image.

BACKGROUND

An ultrasound imaging system may be used to acquire images of a patient's anatomy. Ultrasound imaging systems may acquire a dataset which is then used to generate a 2D image that a medical professional may view and use to diagnose a patient. However, the dataset may include 2D scalar data (e.g., intensity values, power component values, or the like) which results in a flat 2D image that may be more difficult to interpret, thereby increasing a difficulty of diagnosing a patient using the flat 2D image. For example, more complex body structures may be difficult to recognize via a 2D image. As one example, 2D color Doppler images of different body structures may be especially difficult to use for diagnosis.

BRIEF DESCRIPTION

In one embodiment, a method comprises correlating image values of a dataset acquired with an ultrasound imaging system to height values; determining a gradient of the height values; applying shading to a 2D image generated from the dataset using the determined gradient; and displaying the shaded 2D image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood from reading the following description of non-limiting embodiments, with reference to the attached drawings, wherein below.

DETAILED DESCRIPTION

Figure 2:
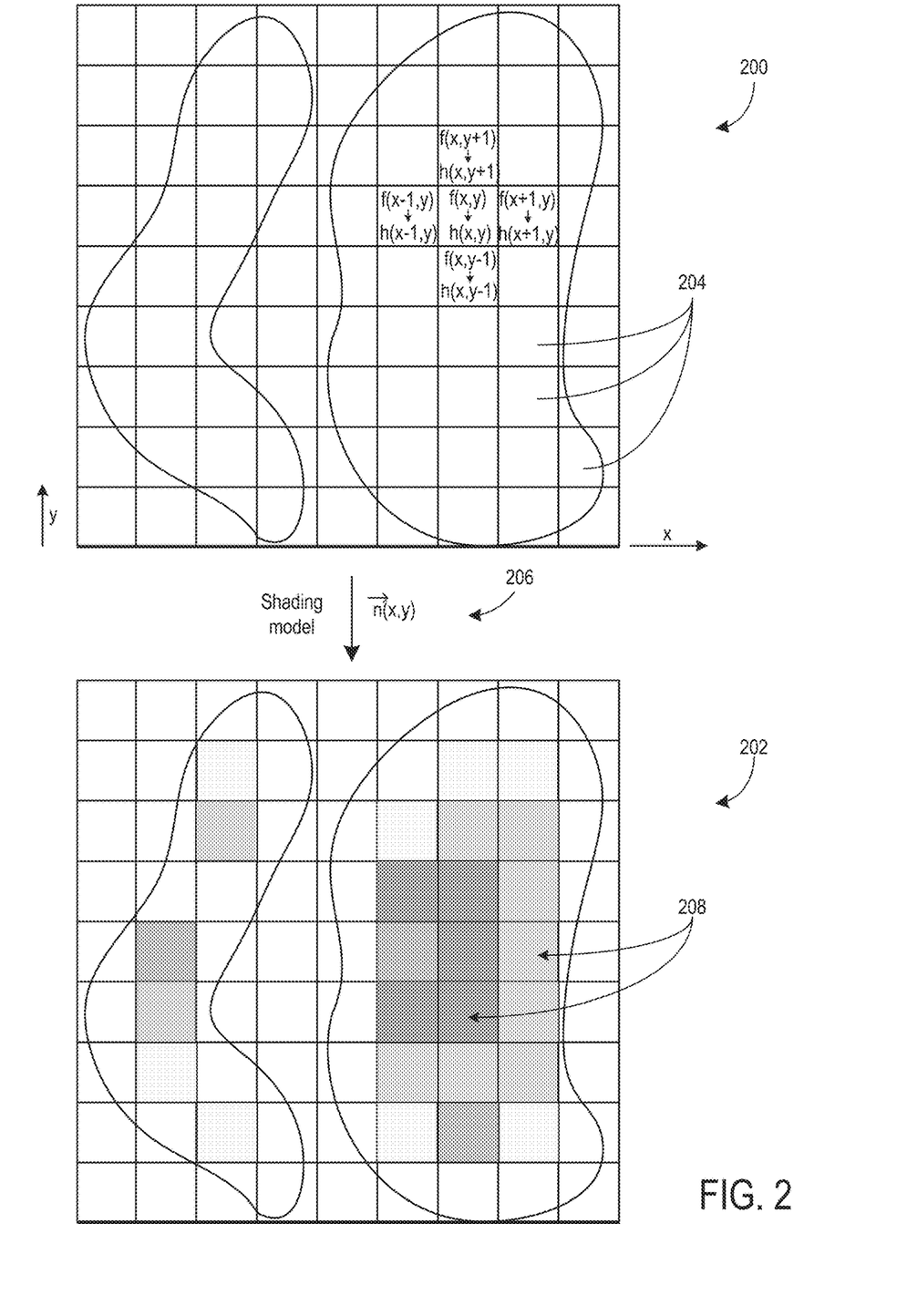
FIG. 2 shows an example of an unshaded 2D ultrasound image generated from an imaging dataset, and additionally shows a shaded 2D ultrasound image generated from the imaging dataset, according to an embodiment of the invention.
Figure 3:
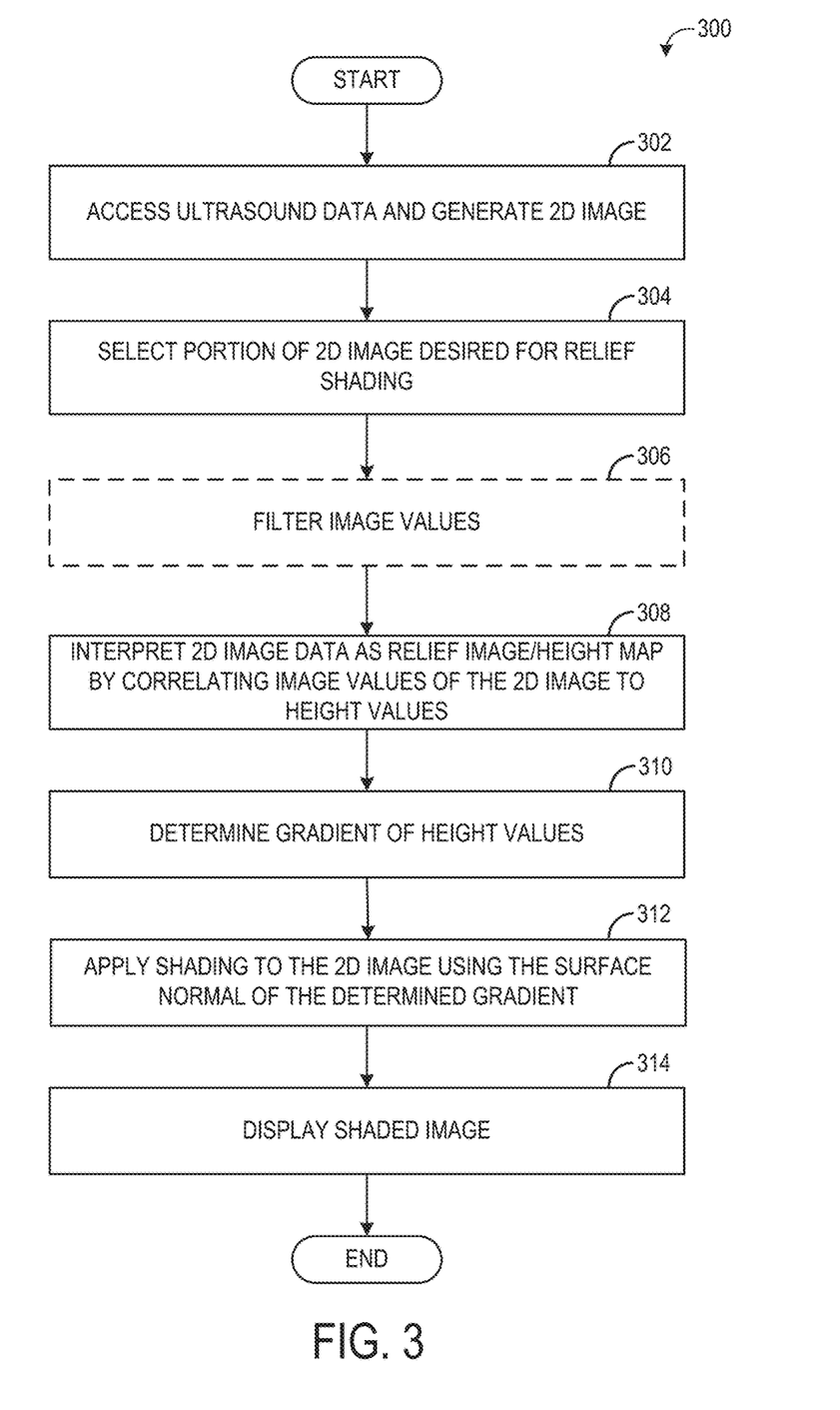
FIG. 3 shows a flow chart of a method for shading a 2D ultrasound image, generated from an ultrasound dataset, using a gradient determined from scalar values of the ultrasound image dataset, according to an embodiment of the invention.
Figure 4:
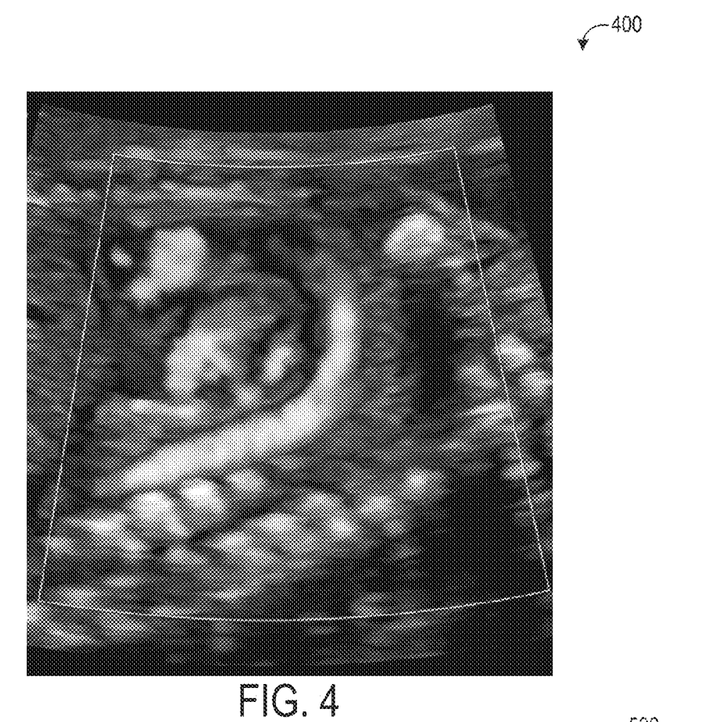
FIG. 4 shows an example of an unshaded 2D. Doppler ultrasound image generated from an imaging dataset, according to an embodiment of the invention.
Figure 5:
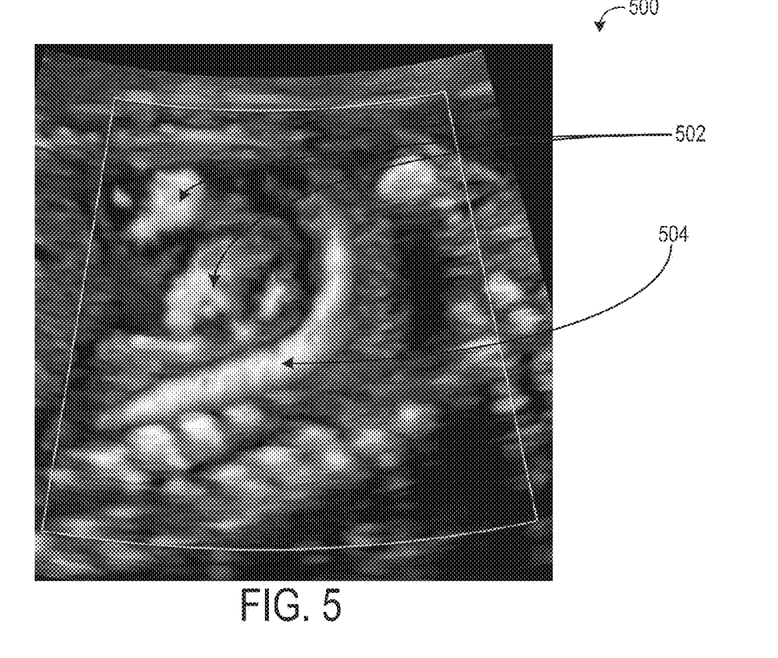
FIG. 5 shows an example of a shaded 2D. Doppler ultrasound image generated from an imaging dataset, according to an embodiment of the invention.
Figure 6:
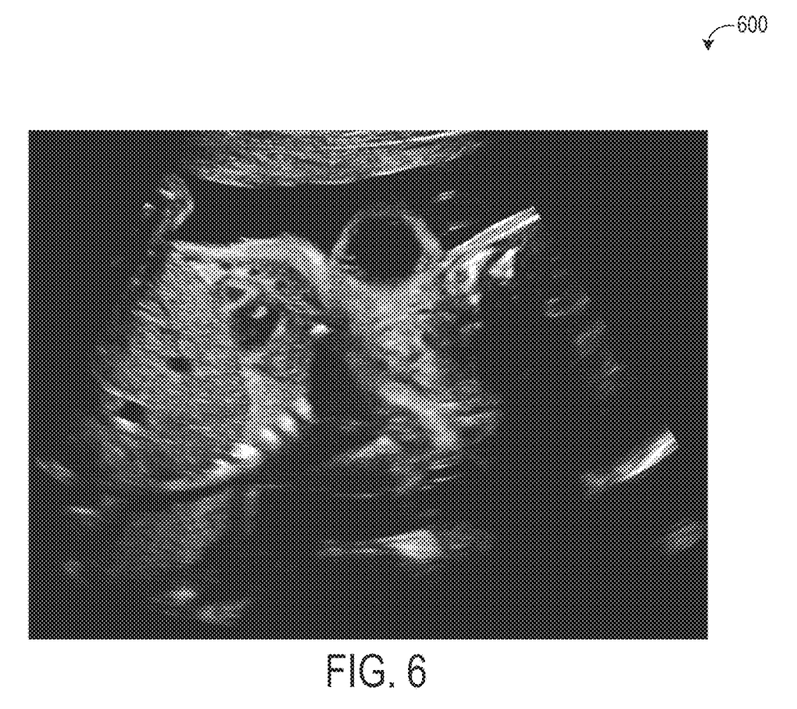
FIG. 6 shows an example of an unshaded 2D B-mode ultrasound image generated from an imaging dataset, according to an embodiment of the invention.

The following description relates to various embodiments of shading a 2D ultrasound image using a gradient determined from height values correlated to image values of an ultrasound imaging dataset (which may be 1D, 2D, or 3D) used to generate the 2D ultrasound image. An ultrasound system, such as the system shown in FIG. 1, may be used to acquire the ultrasound imaging dataset. A 2D image may then be generated using the acquired dataset. An example of a 2D ultrasound image generated from an imaging dataset is shown in FIG. 2. FIG. 2 also shows an example of a shaded 2D ultrasound image where the shading is applied to the 2D ultrasound image using a gradient surface normal determined from image values of the dataset that have been converted to height values. For example, as shown by the method of FIG. 3, image values, such as power or intensity values, of an acquired ultrasound imaging dataset may be converted to height values. A gradient is then determined for the converted height values and shading is applied to the 2D image using the determined gradient. Examples showing a difference between unshaded 2D ultrasound images and shaded 2D ultrasound images (using the method of FIG. 3) are shown by FIGS. 4-7. For example, FIG. 4 shows a first unshaded 2D ultrasound image which may be compared to a first shaded 2D ultrasound image shown by FIG. 5, and FIG. 6 shows a second unshaded 2D ultrasound image which may be compared to a second shaded 2D ultrasound image shown by FIG. 7. In this way, a resulting shaded 2D ultrasound image may have the appearance of depth, thereby making the resulting shaded 2D ultrasound image easier to interpret and, thus, used for patient diagnosis.

Figure 1:
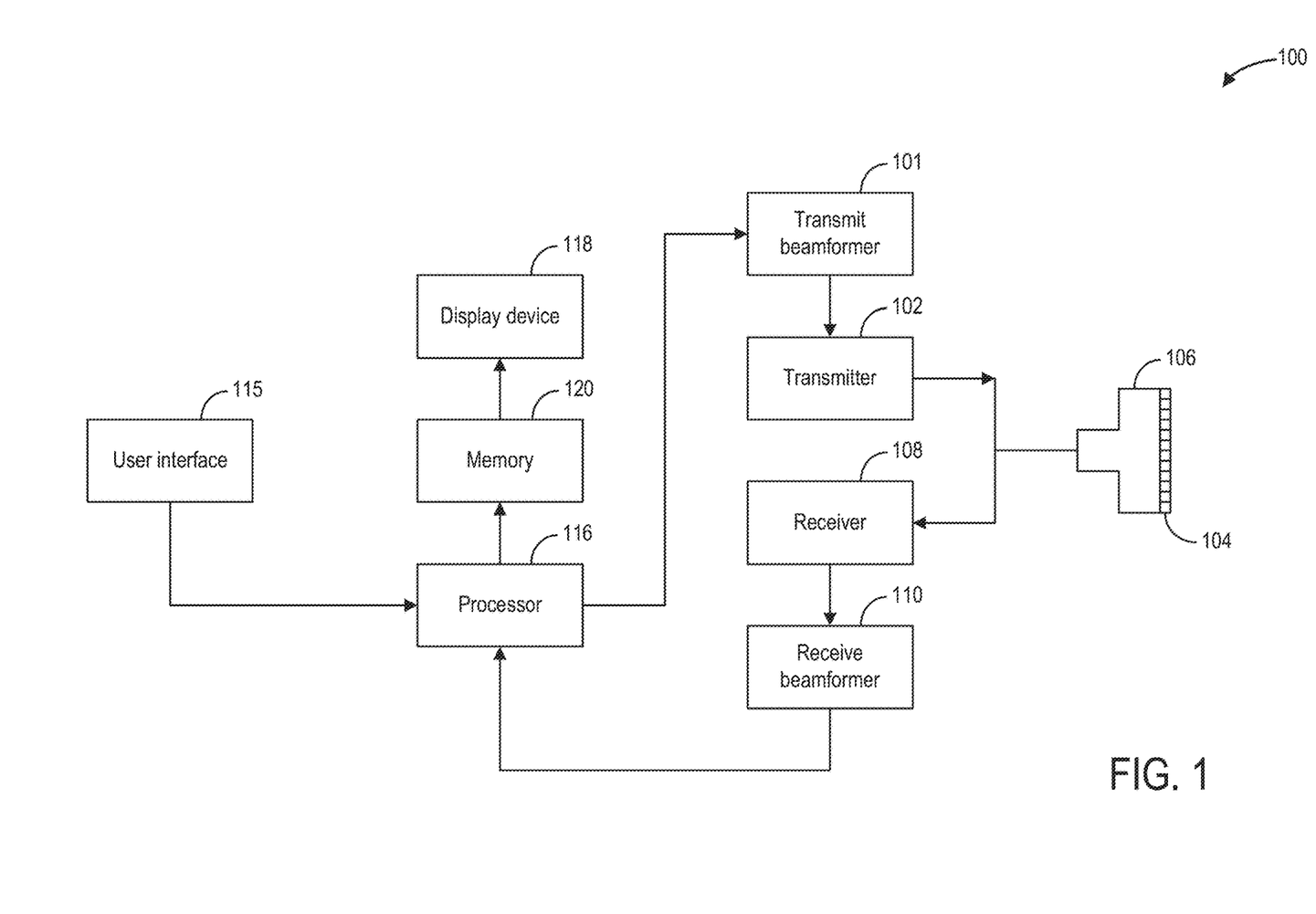
FIG. 1 shows an ultrasound imaging system according to an embodiment of the invention.

Turning now to FIG. 1, a schematic diagram of an ultrasound imaging system 100 in accordance with an embodiment of the invention is seen. The ultrasound imaging system 100 includes a transmit beamformer 101 and a transmitter 102 that drives elements 104 within a transducer array, herein referred to as probe 106, to emit pulsed ultrasonic signals into a body (not shown). According to an embodiment, the probe 106 may be a one-dimensional transducer array probe. However, in some embodiments, the probe 106 may be a two-dimensional matrix transducer array probe. After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

As explained above, in one example, the ultrasound imaging system 100 may be used to acquire an ultrasound imaging dataset (e.g., data). The imaging dataset may include image data, such as intensity data (for B-mode), color or power data (for color Doppler), or the like. For example, an imaging dataset acquired via a color Doppler ultrasound mode (such as color Doppler, power Doppler, Turbulence, Velocity-Power, and Velocity-Turbulence modes) may contain color Doppler data that has a power component. In one example, the imaging dataset may be a 2D dataset (e.g., B-mode data). In another example, the imaging dataset may be a 1D dataset (e.g., motion mode). In yet another example, the imaging dataset may be a 3D/4D dataset (e.g., 3D dataset with an image plane created by slicing through the volume). The processor 116 may generate a 2D ultrasound image from the acquired imaging dataset. For example, the processor 116 may convert the image data of the imaging dataset to brightness (e.g., intensity) values and display an ultrasound image of the acquired dataset as a 2D B-mode image. In another example, the processor 116 may convert the image data of the imaging dataset to color values having a power component and display an ultrasound image of the acquired dataset as a 2D color Doppler image. As explained further below with reference to FIG. 2, the ultrasound image (e.g., 2D color Doppler image, 2D B-mode image, and the like) is comprised of a plurality of pixels, where each pixel is assigned an image value, such as an intensity or color (e.g., power) value. Each value for each pixel is then displayed to form the ultrasound image.

FIG. 2 shows an example of a 2D ultrasound image 200 generated from an imaging dataset acquired with an ultrasound imaging system (such as ultrasound imaging system 100 shown in FIG. 1) and a shaded 2D ultrasound image 202. The 2D ultrasound image 200 includes a plurality of pixels 204 (e.g., each box in images 200 and 202 represents a pixel). The pixels may be of a display screen (e.g., such as display device 118 shown in FIG. 1) which is used to display the 2D ultrasound image 200 and/or the shaded 2D ultrasound image 202. As shown in the 2D ultrasound image 200, the pixels are displayed on a grid having an x-axis (horizontal) and a y-axis (vertical), where each pixel comprises one x unit along the x-axis and one y unit along the y-axis. Thus, each pixel has an x and y value defining its position on the grid. Each pixel of the 2D ultrasound image 200 is assigned an image value (from the acquired imaging dataset). The image value may be a scalar value such as an intensity value (for b-mode images) or a power value (for Doppler images). These image values are represented as a scalar value function, f(x,y), in FIG. 2.

As explained further below, each image value, f(x,y), may be correlated to a height value, h(x,y). Specifically, each image value at each pixel 204 may be converted to a corresponding height value using a relationship (e.g., model). In one example, the relationship for converting each image value to a height value may be a linear relationship. In another example, the relationship or model for converting each image value to a height value may be a monotonic function, such as a logarithmic or sigmoid function that is a function of the image value and then outputs a height value. In some embodiments, the height values (h(x,y), h(x+1, y), etc.) may be used to create a height map or relief image that represents a height field of the 2D image. In this way, the image values may be represented as height values. A gradient may then be calculated for each height value, h(x,y), at each pixel 204.

An example equation for computing the gradient, including a surface normal, is shown by Equation 1:

$$\vec{n}(x,y) = |\nabla h(x,y)| = \left\| \begin{pmatrix} \frac{\partial h}{\partial x} \\ \frac{\partial h}{\partial y} \\ r \end{pmatrix} \right\| = \left\| \begin{pmatrix} h(x-1,y) - h(x+1,y) \\ h(x,y-1) - h(x,y+1) \\ r \end{pmatrix} \right\|$$

In Equation 1, n(x,y) is the surface normal vector at position (x,y) with unit length, ∇ is the gradient, h(x,y) is the scalar height value function (which represents a scalar valued function, such as b-mode intensity, dopper power, or the like) at position (x,y), and r is a constant defining the roughness of the resulting gradient field. The normal of the height value h(x,y) at the position (x,y) is computed by computing the norm of the gradient at this position. The gradient is defined by the partial derivatives in the direction of x and y. The x component is computed with central differences in the x direction. The y component is computed with central differences in the y direction. The z component is the constant r. In this way, determining a gradient for each height value h(x,y) is based on a difference in height values of adjacent pixels 204 in the 2D image 200 (e.g., h(x−1,y), h(x+1,y), h(x,y−1), and h(x,y+1)).

In computing the norm (length=1) of the gradient, the influences of the roughness constant varies for different gradient lengths. For example, if the position (x,y) is in a homogenous region (e.g., a region of the image with little or no variation between height values of adjacent pixels), the x,y components of the gradient are smaller and r is the dominating factor, thereby resulting in a normal vector pointing approximately in the z direction n=(0,0,1). In another example, if the position (x,y) is in a greatly varying area (e.g., a region of the image with larger variation between height values of adjacent pixels), the x and/or the y component of the gradient is bigger and r has less influence, thereby resulting in the normal pointing slightly upwards in the direction of the change. As one example, by representing the image values as height values, computing the gradient of the 2D image includes computing the surface normal of the height field consisting of the height values.

As shown at 206 in FIG. 2, after computing the gradient of each height value, h(x,y), shading (e.g., surface shading) is applied to the 2D ultrasound image 200 using the surface normal vector, n(x,y), at each position (x,y) of the 2D ultrasound image 200. After the application of surface shading using the gradient, the resulting image is the shaded 2D ultrasound image 202 which includes shading 208 at each pixel. The shading model used at 206 may be one or more standard shading models, such as a diffuse specular shading model, a Phong reflection model, a Blinn-Phong shading model, a specular highlight shading model, or the like. As one example, the Phong reflection model (also referred to as Phong illumination, Phong lighting, or Phong shading) is a model of the local illumination of points on a surface (e.g., pixels on the 2D image). The Phong reflection model describes the way a surface reflects light as a combination of the diffuse reflection of rough surfaces with the specular reflection of shiny surfaces. The model also includes an ambient term to account for the small amount of light that is scattered about the entire scene.

FIG. 3 shows a flow chart of a method 300 for shading a 2D ultrasound image (such as 2D ultrasound image 200 shown in FIG. 2), generated from ultrasound data, using a gradient determined from scalar values of the ultrasound image data. Instructions for carrying out method 300 may be executed by a processor (such as processor 116 shown in FIG. 1) based on instructions stored on a memory of the processor (or instructions stored in a memory 120 coupled to processor 116, as shown in FIG. 1) and in conjunction with data received from an imaging system or imaging probe, such as probe 106 described above with reference to FIG. 1. The processor may employ a display device (such as display device 118 shown in FIG. 1) to display a shaded 2D ultrasound image, according to the methods described below.

At 302, the method includes accessing ultrasound data, either previously or currently acquired via an ultrasound probe (such as probe 106 shown in FIG. 1) and generating a 2D ultrasound image from the accessed ultrasound data. In one embodiment, the processor of the ultrasound imaging system (such as processor 116 shown in FIG. 1) accesses an ultrasound imaging dataset (which may be 1D, 2D, or 3D) that is stored in a memory (such as the memory 120 shown in FIG. 1) of the ultrasound imaging system. In another embodiment, the ultrasound data may be accessed in real-time as the data is acquired by the ultrasound probe (e.g., probe 106 shown in FIG. 1). The ultrasound dataset may include image data which includes image values, such as intensity values for B-mode ultrasound or power values (or a power component) for Doppler mode ultrasound. A 2D image may then be generated from the accessed (and/or acquired) ultrasound imaging dataset. As described above with reference to FIG. 2, the 2D image generated from the ultrasound imaging dataset (such as image 200 shown in FIG. 2) may be a flat 2D image.

At 304, the method includes selecting a portion of the 2D image desired for shading (e.g., relief shading). As one example, for a Doppler 2D image, selecting the portion of the 2D image desired for shading may include selecting the color portion (e.g., representing blood flow) of the 2D image. As another example, selecting the portion of the 2D image desired for shading may include selecting an entirety of the 2D image (e.g., such as selecting an entire area of a 2D B-mode image). After selecting the desired portion of the 2D image for shading, the method may optionally continue to 306 to filter the image values of the 2D image. For example, the method at 306 may include having the processor apply a filter to the image values for each pixel in order to smooth the appearance of the 2D image. In some embodiments, filtering of the image values may not be performed and method 300 may instead proceed directly from 304 to 308.

At 308, the method includes interpreting the 2D image data as a relief image (e.g., height map) by correlating the image values of the 2D image to height values. For example, the processor of the ultrasound imaging system may convert the image values of the imaging dataset to height values. As explained above with reference to FIG. 2, each pixel of the 2D image may include an image value, such as an intensity value or a power value (or component). In alternate embodiments, the image value may include a speed value, a brightness value (which may be converted from a color value), an amplitude value, an elasticity value, or the like. Each image value for each pixel may be converted to a height value to create a virtual (e.g., stored in the memory or the processor) height map (e.g., relief image). As one embodiment, the processor may convert the image values for each pixel of the 2D image to height values via a model or relationship stored in the memory of the ultrasound imaging system. For example, the height values may be proportional to image values according to a constant term. In another example, height values may be determined by a function (such as a logarithmic or sigmoid function) of the image values. As another embodiment, a map or look-up table may be stored in the memory which maps image values to height values. As a result, the method at 308 may including looking up and mapping each image value for each pixel to a corresponding height value. The resulting height values may be scalar values.

At 310, the method includes determining a gradient of the determined height values. As explained above with reference to FIG. 2, a gradient may be calculated at each of the pixels of the 2D image. In one embodiment, the processor of the ultrasound imaging system may calculate the gradient of a pixel using the height value of that pixel and the adjacent pixels. Specifically, the gradient for each pixel may be determined according to a relationship or gradient equation (e.g., Equation 1, as explained above with reference to FIG. 1) stored in a memory of the processor of the imaging system that takes into account the height value of the chosen pixel and the height values of the nearest (e.g., left and right) neighbors of the chosen pixel. Calculating the gradient includes calculating a normal of the surface of the pixel. In this way, a gradient surface normal may be determined for each pixel of the 2D image.

After determining the gradient of the height values for each pixel, the method continues to 312 to apply shading to the 2D image using the surface normal of the determined gradient. The processor may calculate shading values for the pixels of the 2D image based on the gradient surface normals. For example, the processor may make a logical determination of the shading value for each pixel based on a shading model stored in memory that is a function of the gradient surface normal. The processor may then apply the determined shading value to the pixel to form a shaded 2D image. As explained above with reference to FIG. 2, the shading model used to apply shading to the 2D image may be one or more standard shading models, such as a diffuse specular shading model, a Phong reflection model, a Blinn-Phong shading model, a specular highlight shading model, or the like. In alternate embodiments, the shading model may be a more complex global model which simulates light propagation with shadowing, and the like. The method at 312 may further include determining a color value for each pixel, according to color data included in the acquired imaging data (e.g., in the case of Doppler imaging). The color value (e.g., red or blue) may be based on a direction of flow, toward or away from the ultrasound probe. Thus, each pixel may have a color value associated with it which is used to color the shaded 2D image. For example, the base color value for each pixel, without shading, may be taken from the original 2D image (generated from the acquired data, as described at 302) and used in the final shaded 2D image. As one example, each pixel may have a velocity value that is converted (e.g., using a look-up table) to a resulting color value (e.g., red or blue). The color value is then shaded (e.g., brightness modulated) according to the normal of the gradient and the light direction.

In some embodiments, the gradient described above may also be used for edge enhancement and segmentation techniques that may then be applied to the 2D ultrasound image.

At 314, the method includes displaying the shaded 2D image. As one example, displaying the shaded 2D image may include displaying the 2D image via a display device (such as display device 118 shown in FIG. 1). In this way, the resulting shaded 2D image may be presented to a user (such as a medical professional) via the display device. Examples of 2D ultrasound images shaded using a gradient determined from height values correlated to ultrasound image data are shown in FIGS. 5 and 7, as described further below.

FIGS. 4 and 5 show an example of a 2D Doppler ultrasound image that is generated using acquired image data that includes color data. Specifically, FIG. 4 shows an unshaded 2D Doppler ultrasound image 400, generated from an imaging dataset. The unshaded 2D Doppler ultrasound image 400 has not been shaded using the gradient surface shading method described herein (e.g., as described above with reference to FIGS. 2 and 3). FIG. 5 shows a shaded 2D Doppler ultrasound image 500, generated from the same imaging dataset as the unshaded 2D Doppler ultrasound image 400 of FIG. 4. However, the shaded 2D Doppler ultrasound image 500 has been shaded using the gradient surface shading method described herein (e.g., described above with reference to FIGS. 2 and 3). In FIG. 5, only the colored portions of the shaded 2D Doppler ultrasound image 500 (e.g., the pixels containing color data) have been shaded according to the gradient surface shading method described herein. Thus, the grayscale portions of FIGS. 4 and 5 may look similar.

As seen in FIG. 4, the unshaded 2D Doppler ultrasound image 400 appears relatively flat with fuzzier edges (at the edge separating the color and grayscale regions). However, the shaded colored regions of the shaded 2D Doppler ultrasound image 500, as seen in FIG. 5, appear crisper at the edges and give the image an appearance of depth (e.g., it looks less flat and has increased contrast relative to the image 400 shown by FIG. 4). Specifically, even though the shaded 2D Doppler ultrasound image 500 is a 2D image generated from 2D image data (e.g., scalar image values), the resulting shaded image has a 3D appearance. As a result, a medical professional may have an easier time recognizing 3D structures, and therefore more complex structures, in the shaded 2D Doppler ultrasound image 500 as compared to the unshaded 2D Doppler ultrasound image 400. For example, color Doppler images of the fetal heart may be more easily interpreted and used for a more accurate patient diagnosis when the images are shaded using the gradient surface shading method described herein (e.g., using height values).

Figure 7:
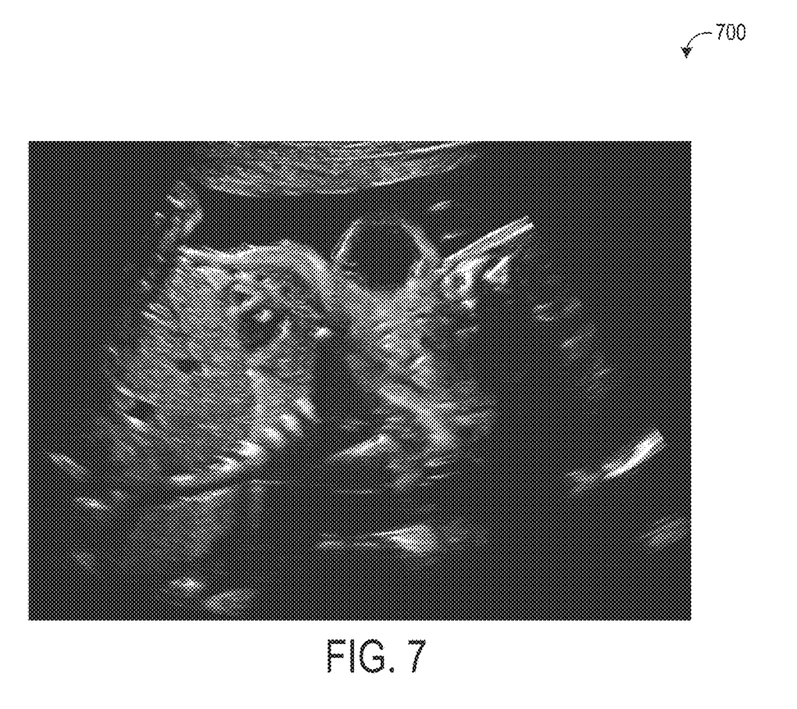
FIG. 7 shows an example of a shaded 2D B-mode ultrasound image generated from an imaging dataset, according to an embodiment of the invention.

FIGS. 6 and 7 show an example of a 2D B-mode ultrasound image that is generated using acquired image data. Specifically, FIG. 6 shows an unshaded 2D B-mode ultrasound image 600, generated from an imaging dataset. The unshaded 2D B-mode ultrasound image 600 has not been shaded using the gradient surface shading method described herein (e.g., as described above with reference to FIGS. 2 and 3). FIG. 7 shows a shaded 2D B-mode ultrasound image 700, generated from the same imaging dataset as the unshaded 2D B-mode ultrasound image 600 of FIG. 6. However, the shaded 2D B-mode ultrasound image 700 has been shaded using the gradient surface shading method described herein (e.g., described above with reference to FIGS. 2 and 3). In FIG. 7, the entire shaded 2D B-mode ultrasound image 700 have been shaded according to the gradient surface shading method described herein.

Similar to as described above with reference to FIGS. 4 and 5, the unshaded 2D B-mode ultrasound image 600 shown in FIG. 6 appears relatively flat with fuzzier edges while the shaded 2D B-mode ultrasound image 700, as seen in FIG. 7, appears crisper and gives the image an appearance of depth (e.g., it looks less flat and has increased contrast relative to the image 600 shown by FIG. 6). Specifically, even though the shaded 2D B-mode ultrasound image 700 is a 2D image generated from 2D image data (e.g., scalar image values), the resulting shaded image has a 3D appearance. As a result, a medical professional may have an easier time recognizing 3D structures, and therefore more complex structures, in the shaded 2D B-mode ultrasound image 700 as compared to the unshaded 2D B-mode ultrasound image 600.

In this way, 2D ultrasound images may be shaded using a gradient determined from height values that are correlated to image data (e.g., scalar image values) of an imaging dataset acquired with a medical imaging system. Shading 2D images in this way may produce 2D images that have a 3D appearance and make complex structures more recognizable to a viewer/medical professional. As a result, these shaded 2D images may be easier to use for diagnosis. Additionally, in the case of Doppler ultrasound images, the image data correlated to the height values for determining the gradient may include a power component of color Doppler image data. By utilizing the power component (as compared to using a different image value, such as intensity for B-mode images) for this gradient shading technique, the resulting shaded images may be more crisp and clear. For example, while the gradient shading technique described herein may be applied to other imaging modes, such as B-mode images, the increased number of structures in B-mode images may make the resulting images less clear as compared to Doppler images. Thus, the gradient shading method described here may be advantageous for Doppler images. The technical effect of correlating image values of a dataset acquired with an ultrasound imaging system to height values, determining a gradient of the height values, applying shading to a 2D image generated from the dataset using the determined gradient, and displaying the shaded 2D image is producing a shaded 2D image that has a 3D appearance and is therefore easier to diagnose with.

As one embodiment, a method comprises: correlating image values of a dataset acquired with an ultrasound imaging system to height values; determining a gradient of the height values; applying shading to a 2D image generated from the dataset using the determined gradient; and displaying the shaded 2D image. In a first example of the method, the dataset includes color data. In a second example of the method, the dataset is a color Doppler dataset and the image values include a power component from the color Doppler dataset. In a third example of the method, the dataset is a B-mode dataset and the image values include intensity values from the B-mode dataset. In one example, correlating image values to the height values includes, for each pixel of the 2D image generated from the dataset, converting an image value to a corresponding height value using a relationship between the image value and the height value. Additionally, determining the gradient of the height values may include determining a separate gradient for each height value of the height values, where each height value is associated with a corresponding pixel, and where the separate gradient for each height value is based on a difference between height values of pixels adjacent to the corresponding pixel within the 2D image. Further, each separate gradient for each height value may include a surface normal, and applying shading to the 2D image may include applying shading to the 2D image using the surface normal of each corresponding pixel of the 2D image.

In another example of the method, displaying the shaded 2D image includes displaying the shaded 2D image via a display screen of the ultrasound imaging system. The method may further comprise accessing the dataset from a memory of the ultrasound imaging system. Additionally, the method may include filtering the image values prior to correlating the image values to height values and determining the gradient. In yet another example, applying shading to the 2D image using the determined gradient includes applying shading to the 2D image based on a shading model which is a function of surface normals of the determined gradient, the shading model including one or more of a diffuse specular shading model, a Phong reflection model, a Blinn-Phong shading model, and a specular highlight shading model.

As another embodiment, a method comprises: accessing a dataset acquired with an ultrasound imaging system, the dataset including a power component for each pixel of a 2D image generated from the dataset; interpreting the 2D image as a relief image by converting the power component for each pixel to a height value; determining a gradient of each height value; shading the 2D image using a surface normal of each determined gradient; and displaying the shaded 2D image. In one example of the method, shading the 2D image includes applying a shading model to the 2D image using the surface normal of each determined gradient, where the shading model includes one or more of a diffuse specular shading model, a Phong reflection model, a Blinn-Phong shading model, and a specular highlight shading model. In another example of the method, the dataset includes color data and the ultrasound imaging system is a color Doppler ultrasound imaging system. Additionally, converting the power component for each pixel to a height value may include selecting pixels of the 2D image that include color data and converting the power component for each selected pixel to the height value. The method may further include not shading pixels of the 2D image that do not contain color data. The method may further include filtering the power component of the selected pixels and converting the filtered power component of each selected pixel to the height value.

As yet another embodiment, an ultrasound imaging system comprises: an ultrasound probe; a display device; and a processor communicatively connected to the ultrasound probe and display device and including instructions stored in memory for: accessing a dataset acquired with the ultrasound probe from the memory; generating a 2D image from the dataset, where each pixel of the 2D image includes a power component; converting the power component of each pixel to a height value; determining a gradient surface normal for each height value; shading the 2D image using the gradient surface normal; and displaying the shaded 2D image via the display device. In one example, the ultrasound imaging system is a color Doppler ultrasound imaging system. In another example, determining the gradient surface normal for each height value includes, for a selected pixel, determining the gradient surface normal for a height value of the selected pixel using central differences and height values of pixels adjacent to the selected pixel.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
generating a flat, 2D image from a 2D dataset including scalar image values without height values, the 2D dataset acquired with an ultrasound imaging system;
determining a gradient of height values from the scalar image values;
applying shading to the flat, 2D image using the determined gradient; and
displaying the shaded flat, 2D image, having a 3D appearance, via a display screen of the ultrasound imaging system, wherein the 2D dataset is a color Doppler dataset and the scalar image values are only a power component from the color Doppler dataset, wherein determining the gradient includes, for each pixel of the flat, 2D image generated from the 2D dataset including the scalar image values, converting a first scalar image value of the scalar image values included in the 2D dataset to a corresponding height value using a relationship between the first scalar image value and the height value, where the relationship is one of a linear relationship or a monotonic function, and where the height value represents a height value of the first scalar image value but does not include height data.

2. The method of claim 1, wherein determining the gradient of the height values includes determining a separate gradient for each height value of the height values, wherein each height value is associated with a corresponding pixel, and wherein the separate gradient for each height value is based on a difference between height values of pixels adjacent to the corresponding pixel within the flat, 2D image.

3. The method of claim 2, wherein each separate gradient for each height value is used to compute a surface normal, and wherein applying shading to the flat, 2D image includes applying shading to the flat, 2D image using the surface normal of each corresponding pixel of the flat, 2D image.

4. The method of claim 1, wherein the color Doppler dataset further includes a velocity value for each pixel of the flat, 2D image, each velocity value converted to a color value, and wherein shading the flat, 2D image includes shading the color value of each pixel of the flat, 2D image using the determined gradient.

5. The method of claim 1, further comprising accessing the 2D dataset from a memory of the ultrasound imaging system.

6. The method of claim 1, further comprising filtering the scalar image values prior to determining the gradient.

7. The method of claim 1, wherein applying shading to the flat, 2D image using the determined gradient includes applying shading to the flat, 2D image based on a shading model which is a function of surface normals of the determined gradient, the shading model including one or more of a diffuse specular shading model, a Phong reflection model, a Blinn-Phong shading model, and a specular highlight shading model.

8. A method, comprising:

accessing a 2D dataset acquired with an ultrasound imaging system via a color Doppler ultrasound mode, the 2D dataset including a scalar, power component value and a velocity value, for each pixel of a flat, 2D image generated from the 2D dataset, the velocity value converted to a color value;

interpreting the flat, 2D image as a relief image by converting the scalar, power component value for each pixel to a height value using a scalar valued function, the converting including selecting pixels of the flat, 2D image that include color data and converting the scalar, power component value for each selected pixel to the height value using the scalar valued function which includes one of a linear function, a logarithmic function, or a sigmoid function;

determining a gradient of each height value;

shading the color value of each pixel of the flat, 2D image using a surface normal of each determined gradient; and displaying the shaded, flat 2D image via a display screen of the ultrasound imaging system.

9. The method of claim 8, wherein shading the color value of each pixel of the flat, 2D image includes applying a shading model to the color value of each pixel of the flat, 2D image using the surface normal of each determined gradient, wherein the shading model includes one or more of a diffuse specular shading model, a Phong reflection model, a Blinn-Phong shading model, and a specular highlight shading model.

10. The method of claim 8, further comprising not shading pixels of the flat, 2D image that do not contain color data and wherein the scalar, power component value is only scalar.

11. The method of claim 8, further comprising filtering the scalar, power component value of the selected pixels and converting the filtered scalar, power component value of each selected pixel to the height value.

12. A color Doppler ultrasound imaging system, comprising:

an ultrasound probe;

a display device; and a processor communicatively connected to the ultrasound probe and the display device and including instructions stored in memory that, when executed during operation of the ultrasound imaging system, cause the processor to:

access a color Doppler 2D dataset, including only 2D scalar data and no 3D data, acquired with the ultrasound probe from the memory;

generate a flat, 2D image from the 2D dataset, where each pixel of the flat, 2D image includes a scalar power component value and a velocity value;

convert the velocity value of each pixel to a color value and convert the scalar, power component value of each pixel to a scalar, height value via a scalar valued function, including selecting pixels of the flat, 2D image that include a color value and converting the scalar, power component value for each selected pixel to the scalar, height value using the scalar valued function which includes one of a linear function, a logarithmic function, or a sigmoid function;

determine a gradient surface normal for each scalar, height value;

shade the color value of each pixel of the flat, 2D image using the gradient surface normal; and display the shaded flat, 2D image via the display device.

13. The ultrasound imaging system of claim 12, wherein determining the gradient surface normal for each scalar, height value includes, for a selected pixel, determining the gradient surface normal for the height value of the selected pixel using central differences and scalar, height values of pixels adjacent to the selected pixel.

* * * * *